United States Patent
Hodgson et al.

(10) Patent No.: US 9,435,194 B2
(45) Date of Patent: Sep. 6, 2016

(54) APPARATUS AND METHOD OF USING AN INLINE ELECTRICAL CONDUCTIVITY MONITOR

(71) Applicants: Schlumberger Technology Corporation, Sugar Land, TX (US); M-I L.L.C., Houston, TX (US)

(72) Inventors: Kim Hodgson, Sugar Land, TX (US); Bruce MacKay, Sugar Land, TX (US); Maxim Yushko, Houston, TX (US); Stephen D. Mason, Katy, TX (US)

(73) Assignees: M-I L.L.C., Houston, TX (US); SCHLUMBERGER TECHNOLOGY CORPORATION, Sugar Land, TX (US)

( * ) Notice: Subject to any disclaimer, the term of this patent is extended or adjusted under 35 U.S.C. 154(b) by 139 days.

(21) Appl. No.: 14/073,925

(22) Filed: Nov. 7, 2013

(65) Prior Publication Data

US 2015/0122488 A1    May 7, 2015

(51) Int. Cl.
*E21B 47/12* (2012.01)
*E21B 47/10* (2012.01)
*E21B 43/26* (2006.01)

(52) U.S. Cl.
CPC .............. *E21B 47/102* (2013.01); *E21B 43/26* (2013.01)

(58) Field of Classification Search
CPC .............. C02F 2209/005; C02F 1/001; C02F 2209/05; E21B 47/102; E21B 47/0007; E21B 47/042; E21B 44/005; E21B 47/12; E21B 49/005; E21B 49/08
See application file for complete search history.

(56) References Cited

U.S. PATENT DOCUMENTS

| | | | |
|---|---|---|---|
| H2228 H | 3/1987 | Eick et al. | |
| 5,736,637 A * | 4/1998 | Evans et al. | ............... 73/152.31 |
| 6,655,221 B1 * | 12/2003 | Aspelund | ............... G01F 1/363 73/861.04 |
| 7,133,786 B1 * | 11/2006 | Dykesteen | ................ G01F 1/58 702/50 |
| 2009/0107666 A1* | 4/2009 | Tchakarov | ............... G01V 3/20 166/250.01 |
| 2011/0140717 A1 | 6/2011 | Wang et al. | |
| 2011/0290492 A1 | 12/2011 | Hodgson et al. | |
| 2013/0144548 A1* | 6/2013 | Xie | ............................... 702/65 |
| 2014/0048491 A1* | 2/2014 | Johnson | ................ C02F 1/5209 210/741 |

* cited by examiner

*Primary Examiner* — Zakiya W Bates
(74) *Attorney, Agent, or Firm* — Rachel E. Greene; Michael L. Flynn; Tim Curington (57) ABSTRACT

A method includes measuring electrical conductivity of a treatment fluid with one or more sensors at various instants of time. The method is further performed by generating one or more signals indicative of the electrical conductivity of the treatment fluid and transmitting the one or more signals to a computer system. The method is further performed by analyzing the one or more signals to determine a phase change in the treatment fluid based upon a positive or negative change in the electrical conductivity of the treatment fluid from a predetermined electrical conductivity range.

18 Claims, 4 Drawing Sheets

APPARATUS AND METHOD OF USING AN INLINE ELECTRICAL CONDUCTIVITY MONITOR

TECHNICAL FIELD

The present disclosure generally relates to evaluating characteristics of a well treatment fluid. More specifically, the present disclosure relates to using an electrical conductivity sensor to directly or indirectly evaluate the conductivity of well treatment fluids in real time when the well treatment fluid is pumped downhole.

BACKGROUND

In oilfield operations, drilling mud is often used while drilling a well to reach a subterranean formation. Drilling mud may also be used to treat the formation to enhance or restore the productivity of the well. The drilling mud is pumped into a drill string to which a drill bit is attached. The drilling mud typically exits the drill string through openings in the drill bit to lubricate the bit and to carry cuttings up an annulus between the drill string and the wellbore for disposal at the surface. Drilling mud, when used as a stimulation treatment, may fall into two main groups, hydraulic fracturing treatments and matrix treatments. Fracturing treatments are performed above the fracture pressure of the formation and create a highly conductive flow path between the reservoir and the wellbore. Matrix treatments are performed below the formation fracture pressure and generally are designed to restore the natural permeability of the formation following damage to the near-wellbore area.

A commonly used method to treat the matrix is "matrix acidizing", which is generally understood in the industry to mean the treatment of the formation with a stimulation fluid containing a reactive acid. In sandstone formations, the acid reacts with the soluble substances in the formation matrix to enlarge the pore spaces. In carbonate formations, the acid dissolves the entire formation matrix. In each case, the matrix acidizing treatment improves the formation permeability to enable enhanced production of formation fluids. Matrix acidizing operations are ideally performed at high rate, but at treatment pressures below the fracture pressure of the formation. This enables the acid to penetrate the formation and extend the depth of treatment while avoiding damage to the formation.

An emulsion of substances may be used as the drilling mud (e.g., oil-based mud or water-based mud) during matrix acidizing. The emulsion is defined by a non-aqueous external phase and an aqueous internal phase. In this drilling mud a non-aqueous "oleaginous" external phase (e.g. oil or synthetic polymers) may be used to inhibit swelling of water-sensitive drill cuttings (e.g. shale). The internal aqueous phase may be one or more acids. For example, typically the reactive acid comprises hydrochloric acid (HCl) and a blend of acid additives. It is also common for acid treatments to include a range of acid types or blends, such as acetic, formic, hydrochloric, hydrofluoric, and fluroboric acids. In addition to the non-aqueous external phase and the aqueous internal phase, compositions of drilling fluids often contain at least trace amounts of chemical emulsifying agents which act to form the non-aqueous external phase emulsions.

Depending on the characteristics of the formation and the treatment fluid, it may be helpful to first emulsify the acid before pumping it down the wellbore. The preparation of acid emulsion is traditionally performed off-site, i.e. at a location that is away from the wellsite, and is generally based on a batch mixing method. Creating the emulsion may be performed by using a tank to recirculate an acid mixture until a complete homogeneous state is achieved. The emulsifying agent is transferred into a batch tank and a pump may be used to recirculate the batch tank until the desired emulsion is created. Once the emulsion is created, the contents of the batch tank can be delivered to the wellsite as a finished product. On-site emulsification may also be performed using a plurality of fluid tanks and a circulation loop, with or without a buffer tank and a pump. The aqueous phase and the non-aqueous phase may be transferred to the circulation loop and therein circulated to mix the aqueous and non-aqueous phases to produce the emulsion. Additives may also be added through fluid tanks or in the circulation loop to enhance emulsification.

Well mixed emulsions penetrate deeper into the formation around the wellbore before the aqueous phase, the acid, begins to react with the formation or the fluid within the formation thereby better enabling recovery of a desired product from the formation and increasing permeability. When emulsions are mixed incorrectly, provided in incorrect ratios, subject to contamination fluids, or subject to certain shear energies, the emulsions may invert. Inversion occurs when the aqueous internal phase becomes continuous and no longer coated by the non-aqueous external phase. When inversion occurs, the acid-in-oil emulsions will have a shorter range of penetration into the wellbore formation, thereby hindering recovery of fluids from the formation.

Currently, when emulsions are pumped into the wellbore, there are no means to detect inversion in real time, and therefore recovery of emulsion quality is hindered by the inability to detect inversion.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one embodiment, a treatment fluid conductivity measuring system is described. The treatment fluid conductivity measuring system has a surface pump, an electrical conductivity sensor, and a computer operably connected to the electrical conductivity sensor. The surface pump is configured to pump a treatment fluid into a well. The electrical conductivity sensor is configured to measure a conductivity of the treatment fluid. The computer has a processor, a non-transitory processor readable medium, and processor executable instructions that when executed cause the processor to cause the electrical conductivity sensor to measure the electrical conductivity of the treatment fluid. The processor then receives a signal or more than one signal indicative of the electrical conductivity of the treatment fluid generated by the conductivity sensor and analyzes the signals to determine a phase change of the treatment fluid based upon a positive or negative change in the electrical conductivity of the treatment fluid. For example, the processor may compare the electrical conductivity of the treatment fluid to a predetermined electrical conductivity range.

In another embodiment, a method is described. The method is performed by measuring an electrical conductivity of a treatment fluid with a conductivity sensor. The conductivity sensor generates a signal or more than one signal indicative of the electrical conductivity of the treatment fluid and transmits the signal or signals to a computer. The method is further performed by analyzing the signal or signals to determine a phase change of the treatment fluid based upon a positive or negative change in the electrical conductivity of the treatment fluid from a predetermined electrical conductivity range.

In yet another embodiment, a method is described and performed by measuring a first electrical conductivity of a treatment fluid with a first conductivity sensor, positioned proximate to a surface of a wellsite, prior to the treatment fluid flowing through a tubing in a well. The method is further performed by measuring a second electrical conductivity of the treatment fluid flowing through the tubing in the well with a second conductivity sensor. The first and second conductivity sensors generate signals indicative of the first and second electrical conductivity of the treatment fluid and transmit the signals to a computer.

DETAILED DESCRIPTION

At the outset, it should be noted that in the development of any such actual embodiment, numerous implementation specific decisions will be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context. Also, in the summary and this detailed description, it should be understood that a range listed or described as being useful, suitable, or the like, is intended to include any within the range, including the end points, and is to be considered as having been stated. For example, "a range from 1 to 10" is to be read as indicating each possible number along the continuum between about 1 and about 10. Thus, even if specific data points within the range, or even no data points within the range, are explicitly identified or refer to a few specific, it is to be understood that the inventors appreciate and understand that any data points within the range are to be considered to have been specified, and that inventors possessed knowledge of the entire range and all points within the range.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or at least one and the singular also includes the plural unless otherwise stated.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Finally, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

Figure 1:
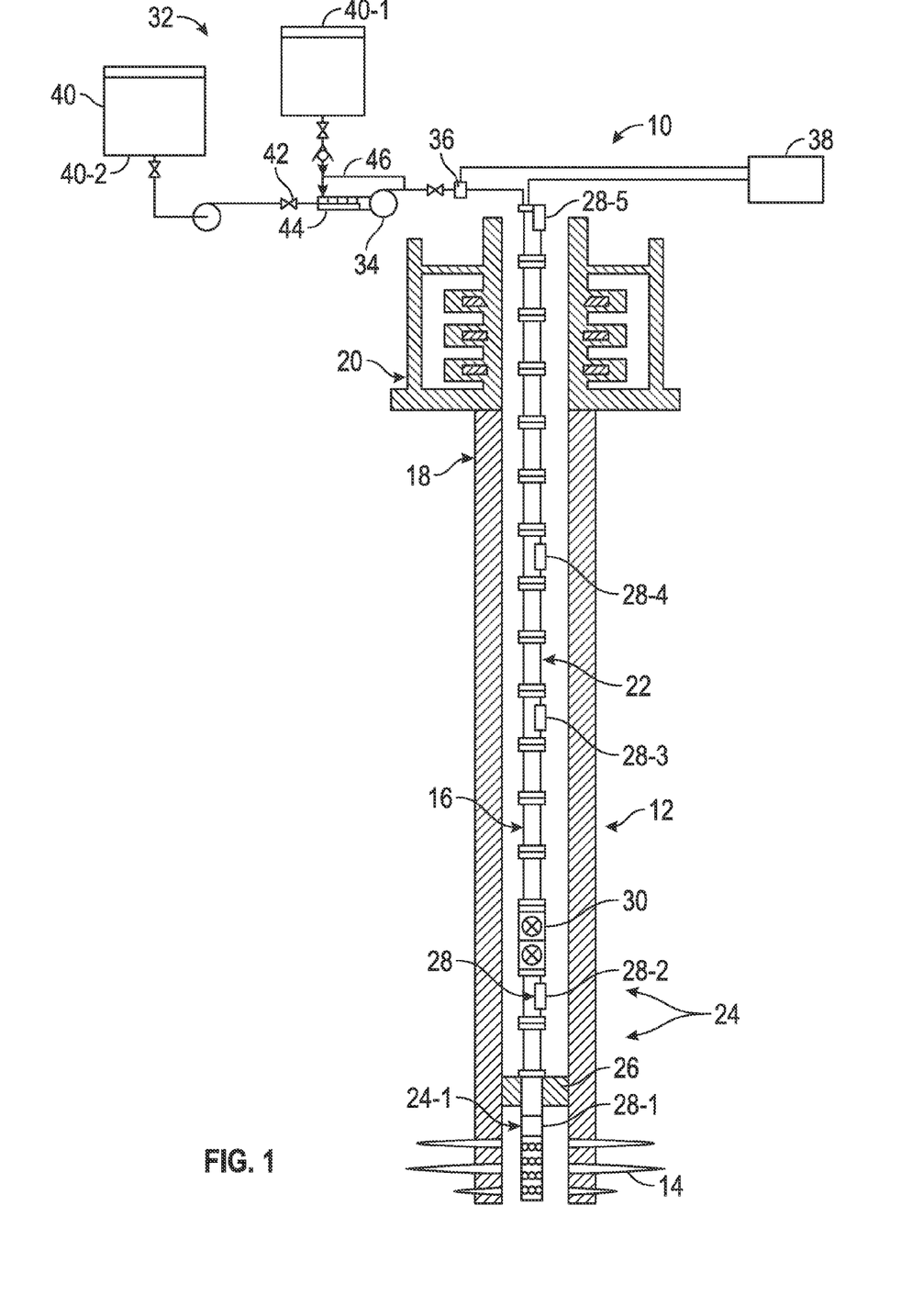
FIG. 1 shows a schematic view of an inline electrical conductivity measurement system in accordance with the present disclosure.

Referring now to FIG. 1, shown therein is a schematic view of a wellsite 10. A well 12 has been drilled through a formation 14 and a drill string 16 extending through the well 12 may be used to extract fluids and other products from the formation 14, as well as to determine various properties of the formation through which the well 12 has been drilled. The well 12 has been lined with a steel casing 18 (cased hole) in the conventional manner, although the well 12 may also be unlined (open hole). At a surface of the well 12, well-head equipment 20 is installed, which may include blow-out preventers and connections for fluid, power, and data communication. The drill string 16 may be formed from tubing 22, such as jointed tubular drill pipe, drill string, production tubing, or the like. The drill string 16 may be outfitted with one or more downhole tool 24, a packer 26 configured to be actuated to seal the wellbore around the drill string 16 above the formation 14, and one or more communication devices 28 enabling communication between the one or more downhole tool 24 and the surface. Downhole equipment 30 may also be outfitted on or around the drill string 16 and may include, but is not limited to additional packers, tester valves, circulation valves, downhole chokes, firing heads, TCP (tube conveyed perforator) gun drop subs, samplers, pressure gauges, downhole flow meters, downhole fluid analyzers, gauge carriers housing multiple tools or collection apparatuses, and the like.

A treatment fluid conductivity measuring system 32 is also shown, having a surface pump 34 to pump a treatment fluid through a fluid path, one or more electrical conductivity sensor 36, and a computer system 38 operably coupled to the one or more electrical conductivity sensor 36 and the downhole tool 24-1. The treatment fluid conductivity measuring system 32 may enable measurement of an electrical conductivity of a treatment fluid used in oilfield operations. In one embodiment, the treatment fluid may a conductive fluid whose properties are to be monitored. For example, the treatment fluid may be an emulsion, for example an acid-in-oil emulsion, used for matrix acidizing, or an emulsion having an aqueous external phase and a non-aqueous internal phase. For example, an acid-in-oil emulsion may be prepared by mixing 15-31% concentration hydrochloric acid with diesel oil or kerosene, such as in a ratio of 70% acid to 30% oil by volume (although other ratios of acid and oils can be used). In one embodiment, the treatment fluid conductivity measuring system 32 may be an inline conductivity measuring system where the one or more electrical conductivity sensor 36 is in fluid communication with the surface pump 34 and is configured to measure the electrical conductivity of the treatment fluid after the emulsion is prepared within the surface pump 34. The one or more electrical conductivity sensor 36, measuring the electrical conductivity of the treatment fluid at various instants of time, may provide information indicating whether the treatment fluid is properly mixed and emulsified or inverted as the electrical conductivity of the treatment fluid is dependent whether the treatment fluid is properly mixed and emulsified. The instants of time can be based upon a schedule, a periodic interval or random intervals. In the example where the treatment fluid is an acid-in-oil emulsion, the electrical conductivity of the treatment fluid will be at or near the electrical conductivity value of the diesel oil if properly mixed, where the diesel oil acts as a non-aqueous external phase and the hydrochloric acid acts as an aqueous internal phase of the emulsion. The electrical conductivity of the treatment fluid will be at or near the electrical conductivity value of the hydrochloric acid if the emulsion has inverted and the aqueous phase has become continuous, meaning the non-aqueous phase is no longer external to the aqueous phase. For example, when the treatment fluid is an acid-in-oil mixture having 12% NaCl and 88% non-aqueous external phase, the conductivity of the properly mixed emulsion varied between 1.37 and 1.42 mS/cm, and the conductivity of the inverted emulsion varied between 40-60 mS/cm. It is believed that the conductivity of a properly mixed emulsion containing hydrochloric acid would be approximately four times more conductive than the conductivity of the properly mixed emulsion containing NaCl.

As shown in FIG. 1, the treatment fluid conductivity measuring system 32 may also be provided with one or more fluid tanks 40, one or more metering valve 42, a sparging manifold 44, and one or more chokes 46. In one embodiment, a first fluid tank 40-1 is provided with a non-aqueous phase having a first predetermined electrical conductivity and a second fluid tank 40-2 is provided with an aqueous phase having a second predetermined electrical conductivity. The treatment fluid, in this embodiment an emulsion of the non-aqueous phase and the aqueous phase is formed by the sparging manifold 44 pre-dispersing the aqueous phase and the non-aqueous phase followed by mixing using the surface pump 34 to produce the treatment fluid emulsion. In some embodiments, the treatment fluid may be premixed and contained in a single fluid tank in fluid communication with the surface pump 34. The one or more electrical conductivity sensor 36 may be configured to measure an electrical conductivity of the treatment fluid, as will be explained in more detail below.

The surface pump 34 may be a centrifugal pump, a vortex pump, an impeller pump, or any other suitable pump capable of mixing the non-aqueous phase and the aqueous phase into an emulsion to form the treatment fluid. In some embodiments, the surface pump 34 may mix additional components, such as stabilizers, surfactants, and other components, along with the non-aqueous phase and the aqueous phase in order to form the treatment fluid.

The one or more electrical conductivity sensor 36 may be implemented as a contact type conductivity sensor or as a non-contact induction conductivity sensor. In embodiments where the one or more electrical conductivity sensor 36 is a contact type conductivity sensor, electrical parts of the one or more electrical conductivity sensor 36 may be placed in contact with the treatment fluid in order to measure the electrical conductivity of the treatment fluid. In other embodiments, the one or more electrical conductivity sensor 36, implemented as a non-contact induction conductivity sensor may employ an inductive method where the electrical parts of the one or more electrical conductivity sensor 36 do not come into contact with the treatment fluid. In this embodiment, the electrical conductivity sensor 36 may have two inductively-coupled coils. A first coil, of the two inductively-coupled coils, may be a driving coil supplied with a predetermined voltage and configured to produce a magnetic field. A second coil, of the two inductively-coupled coils, may form a second coil of a transformer. The treatment fluid may be passed through a channel in the sensor, the channel forming one turn in a winding of the second coil. Passing a treatment fluid through the winding of the second coil may induce a current, which may be output by the sensor as a measurement of the electrical conductivity of the treatment fluid.

Figure 2:
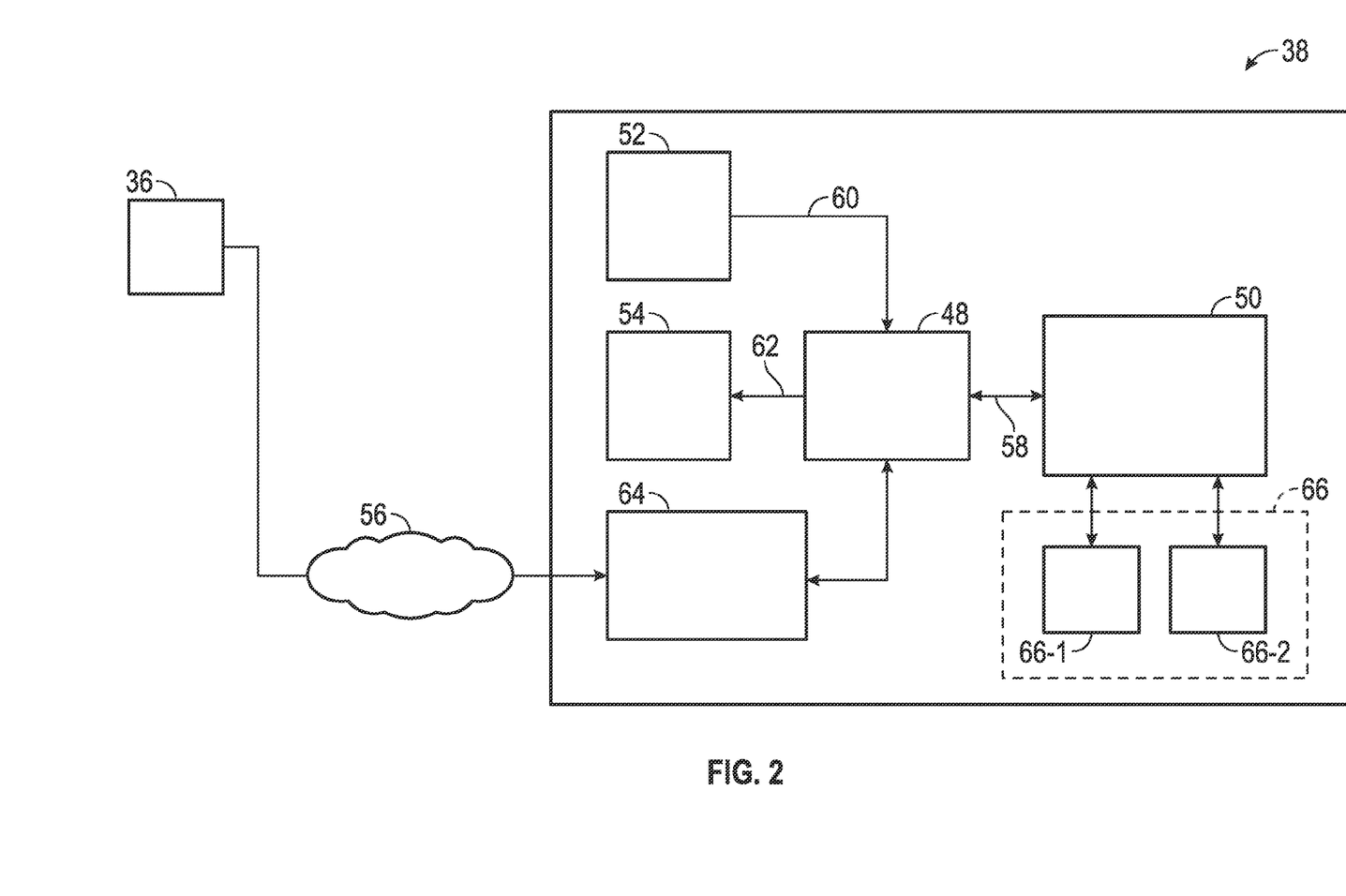
FIG. 2 shows a schematic diagram of hardware and computer executable instructions constructed in accordance with the inventive concepts disclosed herein.

The computer 38 may include at least one processor 48 configured to execute processor executable instructions, a non-transitory processor readable medium 50 capable of storing processor executable instructions, an input device 52, and an output device 54, all of which may be partially or completely network-based or cloud-based, and may not necessarily be located in a single physical location. The computer 38 may be operably coupled to a communications network 56. The computer 38 may be implemented as a smartphone, a tablet, a laptop computer, a personal computer, a desktop computer, a computer terminal, a computer workstation, an e-book reader, a wireless network-capable handheld device, a digital video recorder, a personal digital assistant, or combinations thereof, for example.

The processor 48 may be implemented as a single processor or multiple processors working together to execute processor executable instructions including logic described herein. Exemplary embodiments of the processor 48 may include a digital signal processor (DSP), a central processing unit (CPU), a field programmable gate array (FPGA), a microprocessor, a multi-core processor, a quantum processor, application-specific integrated circuit (ASIC), a graphics processing unit (GPU), a visual processing unit (VPU) and combinations thereof. The processor 48 is operably coupled with the non-transitory processor readable medium 50 via a path 58 which can be implemented as a data bus allowing bi-directional communication between the processor 48 and the non-transitory processor readable medium 50, for example. The processor 48 is capable of communicating with the input device 52 and with the output device 54 via paths 60 and 62 including one or more data busses, for example. The processor 48 may be further capable of interfacing and/or bi-directionally communicating with the one or more electrical conductivity 36 via the network 56, such as by exchanging electronic, digital, analogue, and/or optical signals via one or more physical, virtual, or logical ports using any desired network protocol such as TCP/IP, for example. It is to be understood that in certain embodiments using more than one processor 48, multiple processors may be located remotely from one another, located in the same location, or comprising a unitary multi-core processor (not shown). The processor 48 is capable of reading and/or executing processor executable code stored in the one or more non-transitory processor readable medium 50 and/or of creating, manipulating, altering, and storing computer data structures into the one or more non-transitory processor readable medium 50.

The non-transitory processor readable medium 50 may store an electrical conductivity monitoring program having processor executable instructions. The non-transitory processor readable medium 50 may be implemented as any type of memory, such as random access memory (RAM), a CD-ROM, a hard drive, a solid state drive, a flash drive, a memory card, a DVD-ROM, a floppy disk, an optical drive, and combinations thereof, for example. While the non-transitory processor readable medium 50 may be located in the same physical location as the processor 48, the non-transitory processor readable medium 50 may also be located remotely from the processor 48 and may communicate with the processor 48 via the network 56. Additionally, when more than one non-transitory processor readable medium 50 is used, one or more non-transitory processor readable medium 50 may be located in the same physical location as the processor 48, and one or more non-transitory processor readable medium 50 may be located in a remote physical location from the processor 48. The physical location of the non-transitory processor readable medium 50 can be varied, and the non-transitory processor readable medium 50 may be implemented as a "cloud memory" i. e., one or more non-transitory processor readable medium 50 which is partially, or completely based on or accessed using the network 56, for example. Further, the one or more processor 48 may not communicate directly with the non-transitory processor readable medium 50, but may communicate with another processor 48 communicating with the non-transitory processor readable medium 50 over the network 56, for example.

The input device 52 may pass data to the processor 48, and may be implemented as a keyboard, a mouse, a touchscreen, a camera, a cellular phone, a tablet, a smart phone, a personal digital assistant (PDA), a microphone, a network adapter, and combinations thereof, for example. The input device 52 may also be implemented as a stylus, a mouse, a trackball, and combinations thereof, for example. The input device 52 may be located in the same physical location as the processor 48, or may be remotely located and/or partially or completely network-based.

The output device 54 passes information from the processor 48 to a user in a user perceivable format. For example, the output device 54 can be implemented as a server, a computer monitor, a cell phone, a smartphone, a tablet, a speaker, a website, a PDA, a fax, a printer, a projector, a laptop monitor, and combinations thereof The term "pass" as used herein may refer to either push technology, or to pull technology, and to combinations thereof. The output device 54 can be physically co-located with the processor 48, or can be located remotely from the processor 48, and may be partially or completely network based (e.g., a website). The output device 54 communicates with the processor 48. As used herein the term "user" is not limited to a human, and may comprise a human, a computer, a host system, a smart phone, a tablet, and combinations thereof, for example.

The network 56 may be implemented as a wireless and/or wired network 56 (e.g. the world wide web or Internet, a downhole network, or any other computer network configured to allow bi-directional exchange of data and/or signals between computer processors and/or downhole tools or sensors), and may permit bi-directional communication of information and/or data between the computer 38 and the one or more electrical conductivity sensor 36, for example.

The network 56 may interface with the computer 38 via a communication device 64 and with the one or more electrical conductivity sensor 36 operably coupled with the network 56 in a variety of ways, such as by optical, wireless, wired, acoustic, and/or electronic interfaces, and may use a plurality of network topographies and protocols, such as Ethernet, TCP/IP, circuit switched paths, and combinations thereof, for example. The network 56 may use a variety of network protocols to permit bi-directional interface and communication of data and/or information between the computer 38 and the one or more electrical conductivity sensor 36 operably coupled with the network 56. The network 56 may be secured using any desired secured networking protocol, such as a gateway server, a firewall, data encryption, public or private key cryptography infrastructure, secure socket layer protocol, hypertext transfer protocol secure, a virtual private network, a tunnel, secure shell, and any combinations thereof.

The non-transitory processor readable medium 50 may store processor executable instructions 66. In one embodiment, the processor executable instructions 66 include an electrical conductivity monitoring program 66-1. The non-transitory processor readable medium 50 may also store other processor executable instructions 66-2 such as an operating system and application programs such as a word processor or spreadsheet program, for example. The processor executable instructions for the electrical conductivity monitoring program 66-1 and the other processor executable instructions 66-2 may be written in any suitable high level or low level programming language such as C++, C#, Java, Python, Perl, Binary, assembly language, or other high or low level programming language for example. The electrical conductivity monitoring program 66-1 may be implemented as processor executable instructions, software, firmware, or a combination of software and firmware, for example, and may at least be partially stored on the non-transitory processor readable medium 50. The computer 38 may access and execute the processor executable instructions to execute the electrical conductivity monitoring program 66-1, for example.

Figure 3:
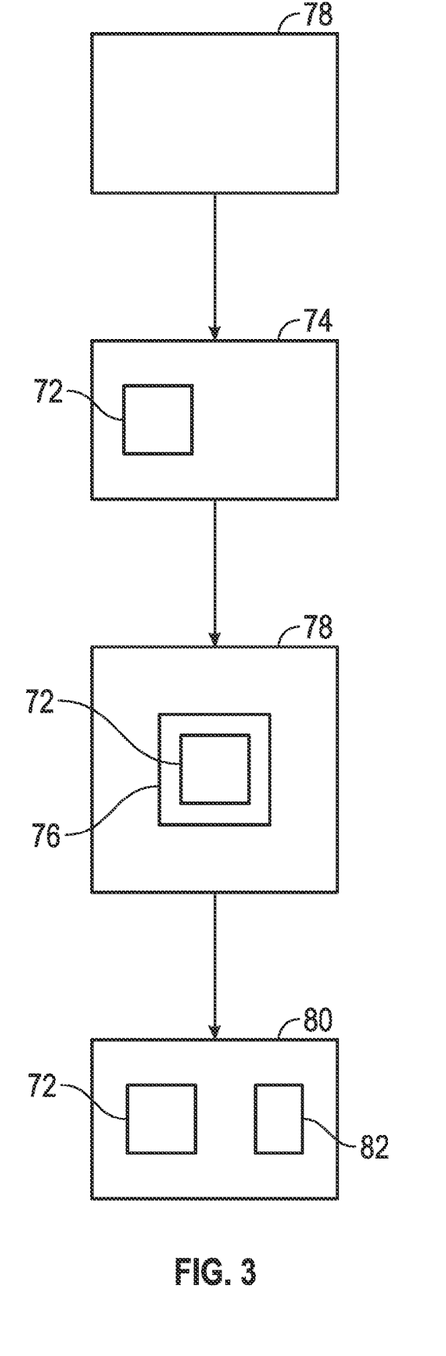
FIG. 3 shows a flow diagram illustrating processor executable instructions for an inline electrical conductivity measurement system.

Referring now to FIG. 3, therein shown is a representation of one embodiment of the electrical conductivity monitoring program 66-1. However, it should be understood that in some embodiments, the processor 48 may be configured to perform the functions of the electrical conductivity monitoring program 66-1, as described below, without the use of the separate electrical conductivity monitoring program 66-1 or the non-transitory processor readable medium 50. For example, the processor 48 may perform the functions of the electrical conductivity monitoring program 66-1 when implemented as an ASIC, as described above. The processor 48 may initiate the electrical conductivity monitoring program 66-1, as indicated by block 70. Once the electrical conductivity monitoring program 66-1 has been initialized, the processor 48 may cause the one or more electrical conductivity sensor 36 to measure an electrical conductivity 72 of the treatment fluid, as indicated by block 74. The processor 48 may receive one or more signal 76 from the one or more electrical conductivity sensor 36, as indicated by block 78. The one or more signal 76 is indicative of the electrical conductivity 72 of the treatment fluid measured by the one or more electrical conductivity sensor 36. The processor 48 may then analyze the one or more signals 76, as indicated by block 80. In one embodiment, analyzing the one or more signal may include comparing the electrical conductivity 72 with a predetermined electrical conductivity range 82. The predetermined electrical conductivity range 82 may be a range encompassing the second predetermined electrical conductivity of the aqueous phase. Comparing the electrical conductivity 72 to the predetermined electrical conductivity range 82 may enable the treatment fluid conductivity measuring system 32 to determine the emulsion quality of the treatment fluid. Where the electrical conductivity 72 is close to or at the value of the first electrical conductivity of the non-aqueous phase, the emulsion of the treatment fluid is well prepared and the non-aqueous phase is external to the aqueous phase, encapsulating the aqueous phase. Where the electrical conductivity 72 is within the range of the predetermined electrical conductivity range 82, the treatment fluid may have inverted where the aqueous phase has become continuous and is no longer properly emulsified with the non-aqueous phase. In other embodiments, the predetermined electrical conductivity range 82 may be indicative of the addition of a contaminant, such as a production fluid, water, or other fluid having an effect on the electrical conductivity 72 of the treatment fluid. In still other embodiments, the predetermined electrical conductivity range 82 may encompass an acceptable range of the electrical conductivity 72 of the treatment fluid, where a positive or negative change beyond the predetermined electrical conductivity range 82 indicates an undesirable change in the treatment fluid. A significant jump in electrical conductivity of the treatment fluid may also indicate an emulsion inversion for an acid-in-oil emulsion.

Figure 4:
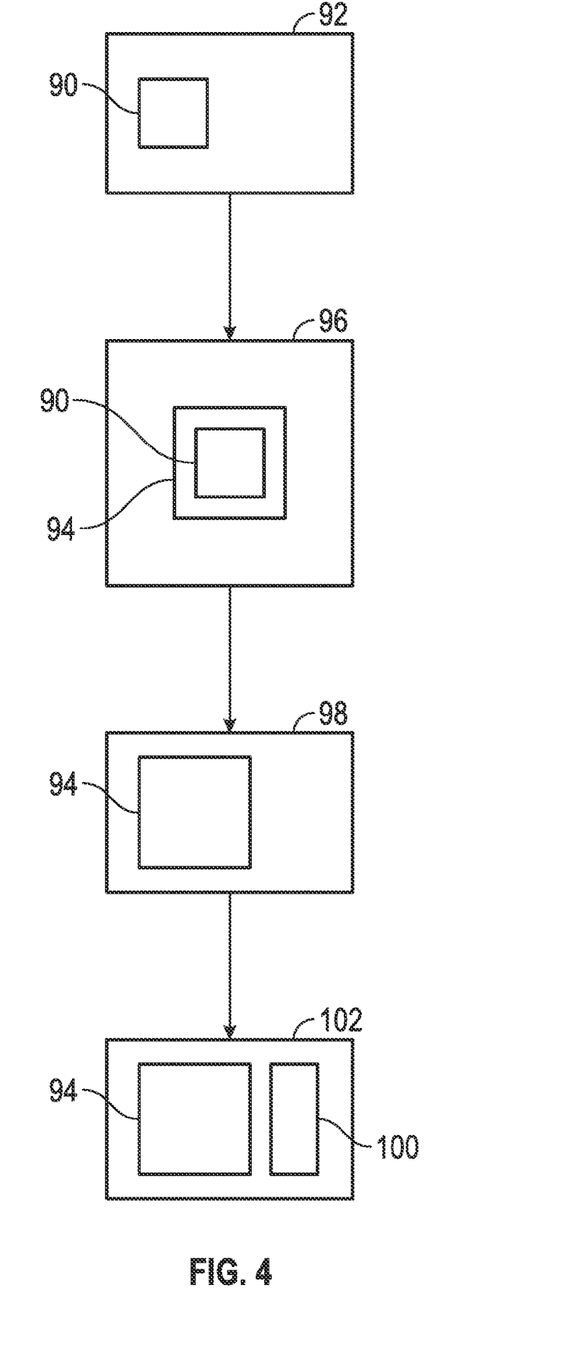
FIG. 4 shows a flow diagram illustrating an embodiment of a method for using an inline electrical conductivity measurement system in accordance with the present disclosure.

Referring now to FIG. 4, in use, the electrical conductivity measuring system 32 may be employed by measuring an electrical conductivity 90 of a treatment fluid with the one or more conductivity sensor 36, as indicated by block 92. The one or more conductivity sensor 36 may generate one or more signal 94 indicative of the electrical conductivity 90 of the treatment fluid, as indicated by block 96. The one or more electrical conductivity sensor 36 may transmit the one or more signal 94 to the computer 38, as indicated by block 98. The computer 38 may analyze the one or more signal 94 to determine a change in the electrical conductivity 90 of the treatment fluid from a predetermined electrical conductivity value range 100, as indicated by block 102, and discussed above. In one embodiment, the one or more conductivity sensor 36 may be positioned proximate to the surface pump 34 to measure the electrical conductivity of the treatment fluid within the surface pump 34. In another embodiment, the one or more conductivity sensor 36 may be positioned proximate to the surface pump 34 to measure the electrical conductivity of the treatment fluid after being mixed or pressurized within the surface pump 34 but prior to being pumped into the well 12. In another embodiment, the one or more conductivity sensor 36 may be positioned within the drill string 16 introduced into the well 12 to measure the electrical conductivity of the treatment fluid flowing within the well 12.

Figure 5:
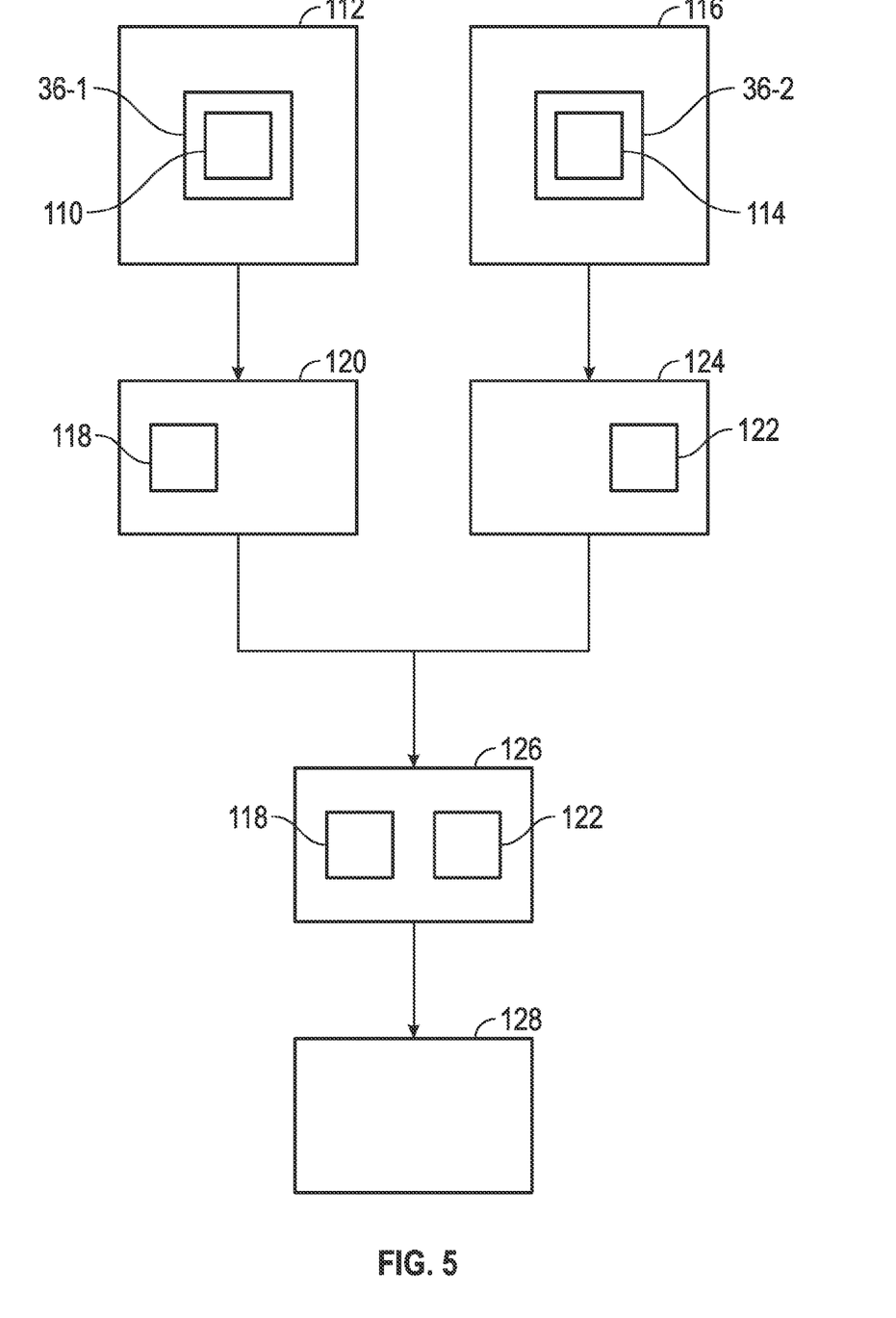
FIG. 5 shows a flow diagram illustrating another embodiment of method for using an inline electrical conductivity measurement system in accordance with the present disclosure.

Referring now to FIG. 5, the one or more conductivity sensor 36 may be implemented as a plurality of conductivity sensors 36. In this embodiment, a first conductivity sensor 36-1 may be positioned proximate to the surface of the well 12 to measure a first conductivity 110 of the treatment fluid prior to the treatment fluid flowing through the drill string 16 within the well 12, as indicated by block 112. In one embodiment, the first conductivity sensor 36-1 may be positioned proximate to or within the surface pump 34. A second conductivity sensor 36-2 may be positioned within the well 12 to measure a second electrical conductivity 114 of the treatment fluid flowing through the pipe 16 within the well 16, as indicated by block 116. The first conductivity sensor 36-1 may generate first signals 118 indicative of the first electrical conductivity 110, as indicated by block 120. The second conductivity sensor 36-2 may generate second signals 122 indicative of the second electrical conductivity 114, as indicated by block 124. The first and second conductivity sensors 36-1 and 36-2 may transmit the first signals 118 and second signals 122, respectively, to the computer system 38, as indicated by block 126. The computer system 38 may then analyze the first and second signals 118 and 122, as indicated by block 128, to determine a change between the first and second electrical conductivity 118 and 122. In some embodiments, the first and second signal 118 or 122 may be analyzed to determine a change between the first or second electrical conductivity 110 or 114 and the predetermined electrical conductivity range 82. The first and second signal 118 and 122 may also be analyzed to determine a change in the electrical conductivity of the treatment fluid between the surface and the well 12, where the first signal 118 and the second signal 122 are indicative of a difference between the first and second electrical conductivities 110 and 114.

The preceding description has been presented with reference to some embodiments. Persons skilled in the art and technology to which this disclosure pertains will appreciate that alterations and changes in the described structures and methods of operation can be practiced without meaningfully departing from the principle, and scope of this application. Accordingly, the foregoing description should be read as consistent with and as support for the following claims, which are to have their fullest and fairest scope.

The scope of patented subject matter is defined by the allowed claims. Moreover, the claim language is not intended to invoke paragraph six of 35 USC §112 unless the exact words "means for" are used. The claims as filed are intended to be as comprehensive as possible, and no subject matter is intentionally relinquished, dedicated, or abandoned.

What is claimed is:

1. A method, comprising:
   measuring an electrical conductivity of a treatment fluid with one or more conductivity sensor;
   generating one or more signals indicative of the electrical conductivity of the treatment fluid;
   transmitting the one or more signals to a computer; and
   analyzing the one or more signals to determine a phase change of the treatment fluid based upon a positive or negative change in the electrical conductivity of the treatment fluid from a predetermined electrical conductivity range;
   wherein the treatment fluid is an emulsion, wherein the one or more conductivity sensor is positioned proximate to a surface pump configured to pump the treatment fluid into a well and wherein the one or more conductivity sensor measures the electrical conductivity of the treatment fluid within the surface pump.

2. The method of claim 1 further comprising positioning a conductivity sensor within a tubing introduced into a well, configured to measure a second electrical conductivity of the treatment fluid flowing through the well.

3. The method of claim 2, wherein measuring the electrical conductivity of the treatment fluid further comprises measuring the first electrical conductivity, of the treatment fluid, proximate to the surface pump and measuring the second electrical conductivity of the treatment fluid flowing through the well, and wherein the one or more signals are indicative of a difference between the first and second electrical conductivities.

4. The method of claim 1, wherein the emulsion is an acid-in-oil emulsion.

5. The method of claim 1, wherein the one or more signals are indicative of a change in the electrical conductivity of the treatment fluid from a predetermined electrical conductivity.

6. A method, comprising:
measuring a first electrical conductivity of a treatment fluid with a first conductivity sensor, positioned proximate to a surface of a wellsite, prior to the treatment fluid flowing through a well;
measuring a second electrical conductivity of the treatment fluid flowing through the tubing within the well with a second conductivity sensor;
generating one or more signals indicative of the first and second electrical conductivity of the treatment fluid; and
transmitting the one or more signals to a computer.

7. The method of claim 6, wherein the treatment fluid is an emulsion.

8. The method of claim 7, wherein the emulsion is an acid-in-oil emulsion.

9. The method of claim 6, wherein the one or more signals are indicative of a change in the electrical conductivity of the treatment fluid from a predetermined electrical conductivity.

10. The method of claim 6, further comprising analyzing the one or more signals to determine a change between the first or second electrical conductivity and a predetermined electrical conductivity range.

11. The method of claim 6 further comprising analyzing the first electrical conductivity and the second electrical conductivity to determine a phase change in the treatment fluid based on the electrical conductivity of the treatment fluid.

12. A treatment fluid conductivity measuring system, comprising:
a surface pump configured to pump a treatment fluid into a well through a fluid path;
one or more electrical conductivity sensor positioned in the fluid path and configured to measure a conductivity of the treatment fluid; and
a computer operably connected to the one or more electrical conductivity sensor, the computer having a processor configured to:
cause the one or more electrical conductivity sensor to measure the electrical conductivity of the treatment fluid;
receive one or more signals indicative of the electrical conductivity of the treatment fluid generated by the one or more conductivity sensor; and
analyze the one or more signals to determine a phase change of the treatment fluid based upon a change in the electrical conductivity of the treatment fluid.

13. The conductivity measuring system of claim 12, wherein the one or more conductivity sensor comprises a first conductivity sensor, positioned proximate to the surface pump, configured to measure a first electrical conductivity of the treatment fluid prior to entering the well and a second conductivity sensor, positioned within a downhole tool in the well, configured to measure a second electrical conductivity of the treatment fluid flowing through the well.

14. The conductivity measuring system of claim 13, wherein analyzing the one or more signals further comprises comparing the first electrical conductivity with the second electrical conductivity to determine a change in the electrical conductivity of the treatment fluid between the surface and within the well.

15. The conductivity measuring system of claim 12, wherein the treatment fluid is an emulsion.

16. The conductivity measuring system of claim 15, wherein the emulsion is an acid-in-oil emulsion.

17. The conductivity measuring system of claim 12, wherein the one or more signals are indicative of a change in the electrical conductivity of the treatment fluid from a predetermined electrical conductivity.

18. The conductivity measuring system of claim 12, wherein analyzing the one or more signals further comprises comparing the electrical conductivity of the well treatment fluid to a predetermined electrical conductivity range.

* * * * *